(12) United States Patent
Kamper et al.

(10) Patent No.: US 10,478,370 B2
(45) Date of Patent: Nov. 19, 2019

(54) ACTUATED GLOVE ORTHOSIS AND RELATED METHODS

(71) Applicant: Rehabilitation Institute of Chicago, Chicago, IL (US)

(72) Inventors: Derek Kamper, Oak Park, IL (US); Kristen Triandafilou, Oak Park, IL (US); Jose Ochoa, Wheaton, IL (US)

(73) Assignee: Rehabilitation Institute of Chicago, Chicago, IL (US)

( * ) Notice: Subject to any disclaimer, the term of this patent is extended or adjusted under 35 U.S.C. 154(b) by 485 days.

(21) Appl. No.: 14/788,563

(22) Filed: Jun. 30, 2015

(65) Prior Publication Data

US 2015/0374575 A1    Dec. 31, 2015

Related U.S. Application Data

(60) Provisional application No. 62/019,135, filed on Jun. 30, 2014.

(51) Int. Cl.
*A61H 1/02* (2006.01)
*A61F 5/01* (2006.01)

(52) U.S. Cl.
CPC .......... *A61H 1/0288* (2013.01); *A61F 5/013* (2013.01); *A61H 2201/123* (2013.01); *A61H 2201/165* (2013.01); *A61H 2201/501* (2013.01); *A61H 2201/5043* (2013.01); *A61H 2201/5048* (2013.01); *A61H 2201/5061* (2013.01); *A61H 2201/5097* (2013.01); *A61H 2230/10* (2013.01); *A61H 2230/60* (2013.01)

(58) Field of Classification Search
CPC ................ A61H 1/0285; A61H 1/0288; A61H 2230/10; A61H 2230/60; A61F 5/0118; A61F 5/013; A61F 2005/0155; A61F 2005/0165; A63B 23/14; A63B 23/16; A63B 21/00178

See application file for complete search history.

(56) References Cited

U.S. PATENT DOCUMENTS 4,644,938 A * 2/1987 Yates .................. A61H 1/0288
482/901
4,875,469 A * 10/1989 Brook .................. A61H 1/0288
482/48

(Continued)

OTHER PUBLICATIONS

C. E. Lang and J. A. Beebe, "Relating movement control at 9 upper extremity segments to loss of hand function in people with chronic hemiparesis," Neurorehabil Neural Repair, 2007, pp. 279-291, 21.

(Continued)

*Primary Examiner* — Joshua Lee
(74) *Attorney, Agent, or Firm* — Polsinelli PC; Ari M. Bai (57) ABSTRACT

An actuated glove orthosis comprises a plurality of digits, each digit configured to be coupled to a finger, each digit defining at least one mechanical stop for preventing hyperextension. The orthosis may further comprise at least one actuator, and a plurality of cables, each cable coupled between a digit and the actuator. Activation of the actuator may increase tension on the plurality of cables to extend the plurality of digits. The device is entirely portable and leaves the hand free to grasp real objects, including as part of a standard therapy session.

17 Claims, 9 Drawing Sheets

(56) References Cited

U.S. PATENT DOCUMENTS

| | | | |
|---|---|---|---|
| 5,115,806 A * | 5/1992 | Greuloch | A61H 1/0288 601/40 |
| 5,327,882 A | 7/1994 | Saringer et al. | |
| 6,502,577 B1 * | 1/2003 | Bonutti | A61F 5/013 128/898 |
| 8,425,438 B2 * | 4/2013 | Fujimoto | A61H 1/0285 482/47 |
| 9,326,909 B2 * | 5/2016 | Liu | A61H 1/0285 |
| 9,375,382 B2 * | 6/2016 | Fausti | A61H 1/0285 |
| 2010/0249676 A1 * | 9/2010 | Kawakami | A61F 5/013 601/40 |
| 2012/0029399 A1 * | 2/2012 | Sankai | A61B 5/04888 601/40 |
| 2012/0059290 A1 * | 3/2012 | Yip | A61H 1/0285 601/40 |
| 2013/0226350 A1 * | 8/2013 | Bergelin | B25J 9/0006 700/275 |
| 2013/0310717 A1 * | 11/2013 | Ranky | A61H 1/0288 601/40 |

OTHER PUBLICATIONS

J. G. Colebatch and S. C. Gandevia, "The distribution of muscular weakness in upper motor neuron lesions affecting the arm," Brain, 1989, pp. 749-763, 112.

S. L. Wolf, P. A. Thompson, C. J. Winstein, J. P. Miller, S. R. Blanton, D. S. Nichols-Larsen, et al., "The EXCITE stroke trial: comparing early and delayed constraint-induced movement therapy," Stroke, 2010, pp. 2309-2315, 41.

S. L. Wolf, C. J. Winstein, J. P. Miller, E. Taub, G. Uswatte, D. Morris, et al., "Effect of constraint-induced movement therapy on upper extremity function 3 to 9 months after stroke: the EXCITE randomized clinical trial," JAMA, 2006, pp. 2095-2104, 296.

S. L. Wolf, H. Newton, D. Maddy, S. Blanton, Q. Zhang, C. J. Winstein, et al., "The Excite Trial: relationship of intensity of constraint induced movement therapy to improvement in the wolf motor function test," Restor Neurol Neurosci, 2007, pp. 549-562, 25.

C. J. Winstein, S. L. Wolf, A. W. Dromerick, C. J. Lane, M. A. Nelsen, R. Lewthwaite, et al., "Interdisciplinary Comprehensive Arm Rehabilitation Evaluation (ICARE): a randomized controlled trial protocol," BMC Neurol, 2013, p. 5, 13.

S. J. Page, P. Levine, A. Leonard, J. P. Szaflarski, and B. M. Kissela, "Modified constraint-induced therapy in chronic stroke: results of a single-blinded randomized controlled trial," Physical Therapy, 2008, pp. 333-340, 88.

D. G. Kamper and W. Z. Rymer, "Quantitative features of the stretch response of extrinsic finger muscles in hemiparetic stroke," Muscle Nerve, 2000, pp. 954-961, 23.

D. G. Kamper, H. C. Fischer, E. G. Cruz, and W. Z. Rymer, "Weakness is the primary contributor to finger impairment in chronic stroke," Arch Phys Med Rehabil, 2006, pp. 1262-1269, 87.

R. K. Powers, J. Marder-Meyer, and W. Z. Rymer, "Quantitative relations between hypertonia and stretch reflex threshold in spastic hemiparesis," Ann Neurol, 1988, pp. 115-124, 23.

D. G. Kamper and W. Z. Rymer, "Impairment of voluntary control of finger motion following stroke: role of inappropriate muscle coactivation," Muscle Nerve, 2001, pp. 673-681, 24.

L. Ada, N. O'Dwyer, and E. O'Neill, "Relation between spasticity, weakness and contracture of the elbow flexors and upper limb activity after stroke: an observational study," Disabil Rehabil, 2006, pp. 891-897, 28.

N. J. Seo, W. Z. Rymer, and D. G. Kamper, "Delays in grip initiation and termination in persons with stroke: effects of arm support and active muscle stretch exercise," J Neurophysiol, 2009, pp. 3108-3115, 101.

N. J. Seo, H. W. Fischer, R. A. Bogey, W. Z. Rymer, and D. G. Kamper, "Use of visual force feedback to improve digit force direction during pinch grip in persons with stroke: a pilot study," Arch Phys Med Rehabil, 2011, pp. 24-30, 92.

C. S. Klein, D. Brooks, D. Richardson, W. E. Mcilroy, and M. T. Bayley, "Voluntary activation failure contributes more to plantar flexor weakness than antagonist coactivation and muscle atrophy in chronic stroke survivors," J Appl Physiol, 2010, pp. 1337-1346, 109.

S.W. Lee, K. Triandafilou, B. A. Lock, and D. G. Kamper, "Impairment in task-specific modulation of muscle coordination correlates with the severity of hand impairment following stroke," PLoS One, 2013, p. e68745, 8.

J. Roh, W. Z. Rymer, E. J. Perreault, S. B. Yoo, and R. F. Beer, "Alterations in upper limb muscle synergy structure in chronic stroke survivors," J Neurophysiol, 2013, pp. 768-781, 109.

J. Stein, L. Bishop, G. Gillen, and R. Helbok, "Robot-assisted exercise for hand weakness after stroke: a pilot study," Am J Phys Med Rehabil, 2011, pp. 887-894, 90.

C. N. Schabowsky, S. B. Godfrey, R. J. Holley, and P. S. Lum, "Development and pilot testing of HEXORR: hand EXOskeleton rehabilitation robot," J Neuroeng Rehabil, 2010, p. 36, 7.

O. Lambercy, L. Dovat, R. Gassert, E. Burdet, C. L. Teo, and T. Milner, "A haptic knob for rehabilitation of hand function," IEEE Trans Neural Syst Rehabil Eng, 2007, pp. 356-366, 15.

P. S. Lum, S. B. Godfrey, E. B. Brokaw, R. J. Holley, and D. Nichols, "Robotic approaches for rehabilitation of hand function after stroke," Am J Phys Med Rehabil, 2012, pp. S242-S254, 91.

N. Yozbatiran, L. Der-Yeghiaian, and S. C. Cramer, "A standardized approach to performing the action research arm test," Neurorehabil Neural Repair, 2008, pp. 78-90, 22.

T. Kaya, A. G. Karatepe, R. Gunaydin, A. Koc, and U. Altundal Ercan, "Inter-rater reliability of the Modified Ashworth Scale and modified Modified Ashworth Scale in assessing poststroke elbow flexor spasticity," Int J Rehabil Res, 2011, pp. 59-64, 34.

R. W. Bohannon and M. B. Smith, "Interrater reliability of a modified Ashworth scale of muscle spasticity," Phys Ther, 1987, pp. 206-207, 67.

G. Uswatte, E. Taub, D. Morris, M. Vignolo, and K. McCulloch, "Reliability and validity of the upper-extremity Motor Activity Log-14 for measuring real-world arm use," Stroke, 2005, pp. 2493-2496, 36.

C. E. Lang, J. R. MacDonald, D. S. Reisman, L. Boyd, T. Jacobson Kimberley, S. M. Schindler-Ivens, et al., "Observation of amounts of movement practice provided during stroke rehabilitation," Arch Phys Med Rehabil, 2009, pp. 1692-1698, 90.

F. Buma, G. Kwakkel, and N. Ramsey, "Understanding upper limb recovery after stroke," Restor Neurol Neurosci, 2013, pp. 707-722, 31.

G. Kwakkel, "Impact of intensity of practice after stroke: issues for consideration," Disabil Rehabil, 2006, pp. 823-830, 28.

J. H. Lin, M. J. Hsu, C. F. Sheu, T. S. Wu, R. T. Lin, C. H. Chen, et al., "Psychometric comparisons of 4 measures for assessing upper-extremity function in people with stroke," Phys Ther, 2009, pp. 840-850, 89.

R. H. Nijland, E. E. Van Wegen, B. C. Harmeling-Van Der Wel, G. Kwakkel, and E. Investigators, "Presence of finger extension and shoulder abduction within 72 hours after stroke predicts functional recovery: early prediction of functional outcome after stroke: the EPOS cohort study," Stroke, 2010, pp. 745-750, vol. 41.

C. E. Lang, S. L. Dejong, and J. A. Beebe, "Recovery of thumb and finger extension and its relation to grasp performance after stroke," J Neurophysiol, 2009, pp. 451-459, 102.

K. M. Triandafilou, H. C. Fischer, J. D. Towles, D. G. Kamper, and W. Z. Rymer, "Diminished capacity to modulate motor activation patterns according to task contributes to thumb deficits following stroke," J Neurophysiol, 2011, pp. 1644-1651, 106.

C. Patten, E G.Condliffe, C. A. Dairaghi, and P. S. Lum, "Concurrent neuromechanical and functional gains following upper-extremity power training post-stroke," J Neuroeng Rehabil, 2013, p. 1, 10.

C. Stinear, S. Ackerley, and W. Byblow, "Rehabilitation is initiated early after stroke, but most motor rehabilitation trials are not: a systematic review," Stroke, 2013, pp. 2039-2045, 44.

Saebo [Catalog], 2011.

(56) References Cited

OTHER PUBLICATIONS

Saebo [Brochure], n. d.
Saebo, "What is the SaeboFlex", Retrieved from https://web.archive.org/web/20130830185918/http://www.saebo.com/products/saeboflex/.
C. Brăilescu, et al.,"A study regarding the results of a rehabilitation program in patients with traumatic lesions of the hand after surgery," Palestrica of the third millennium—Civilization and Sport, 2013, pp. 263-270, 14(4).
D. Bullen, "Intelligent Design: Robotic technology inspires higher levels of function following stroke and brain injury," ADVANCE for Occupational Therapy Practitioners, 2014, pp. 10-12, www.advanceweb.com/ot.
Kinetec Maestra [Manual] pp. 2-20.
Kinetec [Brochure], 2014.
K. Triandafilou, et al., "Transient Impact of Prolonged Versus Repetitive Stretch on Hand Motor Control in Chronic Stroke," Top Stroke Rehabil, 2011, pp. 316-324,18(4).
N. G. Kutner, et al., "Quality-of-Life Change Associated With Robotic-Assisted Therapy to Improve Hand Motor Function in Patients With Subacute Stroke: A Randomized Clinical Trial," Physical Therapy, 2010, pp. 493-504, 90(4).
Chedoke McMaster Stroke Assessment, Development, Validation and Administration Manual (Oct. 2008).
K. M. Triandafilou, J. Ochoa, X. Kang, H. C. Fischer, M. E. Stoykov, and D. G. Kamper, "Transient impact of prolonged versus repetitive stretch on hand motor control in chronic stroke," Top Stroke Rehabil, vol. 18, pp. 316-324, Jul.-Aug. 2011.
K. M. Triandafilou, J. M. Ochoa, and D. G. Kamper, "Effect of static versus cyclical stretch on hand motor control in subacute stroke.," Int J Neurorehabilitation, vol. 1, pp. 124-128, 2014.
K. M. Triandafilou and D. G. Kamper, "Carryover effects of cyclical stretching of the digits on hand function in stroke survivors," Arch Phys Med Rehabil, vol. 95, pp. 1571-1576, Aug. 2014.
B. T. Iwamuro, H. C. Fischer, and D. G. Kamper, "A pilot study to assess use of passive extension bias to facilitate finger movement for repetitive task practice after stroke," Top Stroke Rehabil, vol. 18, pp. 308-315, Jul.-Aug. 2011.
E. G. Cruz and D. G. Kamper, "Use of a novel robotic interface to study finger motor control," Ann Biomed Eng, vol. 38, pp. 259-268, Feb. 2010.
D. G. Kamper and W. Zev Rymer, "Effects of geometric joint constraints on the selection of final arm posture during reaching: a simulation study," Exp Brain Res, vol. 126, pp. 134-138, May 1999.
T. M. Sukal, M. D. Ellis, and J. P. Dewald, "Shoulder abduction-induced reductions in reaching work area following hemiparetic stroke: neuroscientific implications," Exp Brain Res, vol. 183, pp. 215-223, Nov. 2007.
S. Barreca, C. K. Gowland, P. Stratford, M. Huijbregts, J. Griffiths, W. Torresin, et al., "Development of the Chedoke Arm and Hand Activity Inventory: theoretical constructs, item generation, and selection," Top Stroke Rehabil, vol. 11, pp. 31-42, Fall 2004.
J. W. Krakauer, "Avoiding performance and task confounds: multimodal investigation of brain reorganization after stroke rehabilitation," Exp Neurol, vol. 204, pp. 491-495, Apr. 2007.
Abstract of Carey Jr. Manual stretch: Effect of finger movement control and force control in stroke subjects with spastic extrinsic finger flexor muscles. Archives of Phys Med Rehabil 1990; 71: 888-894.
Abstract of Chae J. Neuromuscular electrical stimulation for motor relearning in hemiparesis. Phys Med Rehabil Clin N Am 2003; 14: S93-109.
Hartman-Maeir A, Soroker N, Ring H, Avni N, Katz N. Activities, participation and satisfaction one-year post stroke. Disabil Rehabil 2007; 29: 559-66.
Abstract of Rose V, Shah S. A comparative study on the immediate effects of hand orthoses on reduction of hypertonus, Aust Occup Ther J 1987; 34: 59-64. X.
J. A. Beebe and C. E. Lang, "Active range of motion predicts upper extremity function 3 months after stroke," Stroke, vol. 40, pp. 1772-1779, May 2009.

E.B. Brokaw et al, Hand Spring Operated Movement Enhancer (HandSOME): A Portable, Passive Hand Exoskeleton for Stroke Rehabilitation, IEEE Transactions on Neural Systems and Rehabilitation Engineering, vol. 19, No. 4, pp. 391-399, Aug. 2011.
Ada L., Goddard E., McCully J., Stavrinos T., Bampton J., "Thirty minutes of positioning reduces the development of shoulder external rotation contracture after stroke: A randomized controlled trial," Archives of Phys Med and Rehabil, 2005, pp. 230-234, 86.
Beckley M.N., "Community participation following cerebrovascular accident: impact of the buffering model of social support," Am J Occup Ther, 2006, pp. 129-135, 60.
Bhatt E., Nagpal A., Greer K.H., Grunewald T.K., Steele J.L., Wiemiller J.W., Lewis S.M., Carey J.R., "Effect of finger tracking combined with electrical stimulation on brain reorganization and hand function in subjects with stroke," Exp Brain Res, 2007, pp. 435-447, 182.
Bonifer N. and Anderson K.M., "Application of constraint-induced movement therapy for an individual with severe chronic upper-extremity hemiplegia," Phys Therapy, 2003, pp. 384-398, 83.
Bressel E. and McNair P.J., "The effect of prolonged static and cyclic stretching on ankle joint stiffness, torque relaxation, and gait in people with stroke," Phys Ther, 2002, pp. 880-887, 82.
Damon B.M., Wigmore D.M., Ding Z., Gore J.C., Kent-Braun J.A., "Cluster analysis of muscle functional MRI data," J Appl Physiol, 2003, pp. 1287-1296, 95.
Gowland C., Stratford P., Ward M., Moreland J., Torresin W., Van Hullenaar S., et al., "Measuring physical impairment and disability with the Chedoke-McMaster Stroke Assessment," Stroke, 1993, pp. 58-63, 24.
Gracies J.M., Morosszeky J.E., Renton R., Sandanam J., Gandevia S.C., Burke K., "Short-term effects of dynamic lycra splints on upper limb in hemiplegic patients," Archives Phys Med Rehabil, 2000, pp. 1547-1555, 81.
Harris-Love M.L. and Cohen L.G., "Noninvasive cortical stimulation in neurorehabilitation: a review," Arch Phys Med Rehabil, 2006, pp. S84-S93, 87.
Hartman-Maeir A., Eliad Y., Kizoni R., Nahaloni I., Kelberman H., Katz N., "Evaluation of a long-term community based rehabilitation program for adult stroke survivors," NeuroRehabilitation, 2007, pp. 295-301, 22.
Harvey L., De Jong I., Goehl G., Marwedel S., "Twelve weeks of nightly stretch does not reduce thumb web-space contractures in people with a neurological condition: A randomized controlled trial," Aust J of Physiotherapy, 2006, pp. 251-258, 52.
Horsley S.A., Herbert R.D., Ada L., "Four weeks of daily stretch has little or no effect on wrist contracture after stroke: A randomized controlled trial," Aus J of Physiotherapy, 2007, pp. 239-245, 53.
Jack D., Boian R., Merians A.S., Tremaine M., Burdea G.C., Adamovich S.V., Recce M., Poizner H., "Virtual reality-enhanced stroke rehabilitation," IEEE Trans Neural Syst Rehabil Eng, 2001, pp. 308-318, 9.
Kamper D.G., Harvey R.L., Suresh S., Rymer W.Z., "Relative contributions of neural mechanisms versus muscle mechanics in promoting finger extension deficits following stroke," Muscle Nerve, 2003, pp. 309-318, 28.
Kinugasa R., Kawakami Y., Fukunaga T., "Mapping activation levels of skeletal muscle in healthy volunteers: an MRI study," J Magn Reson Imaging, 2006, pp. 1420-1425, 24.
Kinugasa R., Kawakami Y., Fukunaga T., "Quantitative assessment of skeletal muscle activation using muscle functional MRI," J Magn Reson Imaging, 2006, pp. 639-644, 24.
Kleim J.A., Jones T.A., Schallert T., "Motor enrichment and the induction of plasticity before or after brain injury," Neurochem Res, 2003, pp. 1757-1769, 28.
O'Connor K.M., Price T.B., Hamill J., "Examination of extrinsic foot muscles during running using mfMRI and EMG," J Electromyogr Kinesiol, 2006, pp. 522-530, 16.
Selles R.W., Li X., Lin F., Chung S.G., Roth E.J., Zhang L.Q., "Feedback-controlled and programmed stretching of the ankle plantarflexors and dorsiflexors in stroke: Effects of a 4-week intervention program," Archives of Phys Med and Rehabil, 2005, pp. 2330-2336, 86.

(56) References Cited

OTHER PUBLICATIONS

Law M., Russell D., Pollock N., Rosenbaum P., Walter S., King G., "A comparison of intensive neurodevelopmental therapy plus casting and a regular occupational therapy program for children with cerebral palsy," Dev Med Child Neurol, 1997, pp. 664-670, 39.
Liepert J., Bauder H., Wolfgang H.R., Miltner W.H., Taub E., Weiller C., "Treatment-induced cortical reorganization after stroke in humans," Stroke, 2000, pp. 1210-1216, 31.
Mathiowetz V., Volland G., Kashman N., Weber K., "Adult norms for the Box and Block Test of manual dexterity," Am J Occup Ther, 1985, pp. 386-391, 39.
McDonnell M.N., Hillier S.L., Miles T.S., Thompson P.D., Ridding M.C., "Influence of combined afferent stimulation and task-specific training following stroke: a pilot randomized controlled trial," Neurorehabil Neural Repair, 2007, pp. 435-443, 21.
Mennemeyer S.T., Taub E., Uswatte G., Pearson S., "Employment in households with stroke after Constraint-Induced Movement therapy," NeuroRehabilitation, 2006, pp. 157-165, 21.
Rosamond W., Flegal K., Friday G., Furie K., et a.l., "Heart disease and stroke statistics—2007 update: a report from the American Heart Association Statistics Committee and Stroke Statistics Subcommittee," Circulation, 2007, pp. e69-e171,115.
Sheehan J.L., Winzeler-Mercay U., Mudie M.H., "A randomized controlled pilot study to obtain the best estimate of the size of the effect of a theramoplastic resting splint on spasticity in the stroke-affected wrist and fingers," Clin Rehabil, 2006, pp. 1032-1037, 20.
Simone, L.K., Sundarrajan N., Luo X., Jia Y., Kamper D.G., "A low cost instrumented glove for extended monitoring and functional hand assessment," J Neurosci Methods, 2007, pp. 335-348, 160.
Takahashi C.D., Der-Yeghiaian L., Le V., Motiwala R.R., Cramer S.C., "Robot-based hand motor therapy after stroke," Brain, 2008, pp. 425-437, 131.
Thom T., Haase N., Rosamond W., Howard V.J., Rumsfeld J., et al., "Heart disease and stroke statistics—2006 update: a report from the American Heart Association Statistics Committee and Stroke Statistics Subcommittee," Circulation, 2006, pp. e85-e151, 113.
Turton A.J. and Britton E., "A pilot randomized controlled trial of a daily muscle stretch regime to prevent contractures in the arm after stroke," Clin Rehabil, 2005, pp. 600-612, 19.
Wu C., Huang M.H., Less C.L., Liu C.W., Lin L.J., Chen C.H., "Effect of spasticity after performance of dynamic-repeated passive ankle joint motion exercise in chronic stroke patients," Kaohsiung J Med Sci, 2006, pp. 610-617, 22.
Yeh C.Y., Chen J.J., Tsai K.H., "Quantifying the effectiveness of the sustained muscle stretching treatments in stroke patients with ankle hypertonia," J Electromyogr Kinesiol, 2007, pp. 453-461, 17.
Yili F., et al., "Design and Development of a Hand Rehabilitation Robot for Patient-cooperative Therapy Following Stroke," IEEE International Conference on Mechatronics and Automation, 2011, pp. 112-117, Beijing, China.
Ho, N.S.K., Tong K.Y., et al., "An EMG-driven exoskeleton hand robotic training device on chronic stroke subjects," IEEE International Conference on Rehabilitation Robotics, 2011, pp. 1-5.
Dovat, L., et al., "HandCARE: a cable-actuated rehabilitation system to train hand function after stroke," IEEE Trans Neural Syst Rehabil Eng., 2008, pp. 582-591, 16(6).
Yeow, C.H., et al., "Cable-Driven Finger Exercise Device With Extension Return Springs for Recreating Standard Therapy Exercises," Journal of Medical Devices, 2014, pp. 1-7, 8.
J. A. Rathelot and P. L. Strick, "Muscle representation in the macaque motor cortex: ananatomical perspective," Proc Natl Acad Sci USA, 2006, pp. 8257-8262, 103.
J. Armand, et al., "Postnatal development of corticospinal projections from motor cortex to the cervical enlargement in the macaque monkey," J Neurosci, 1997, pp. 251-266, 17.
C. E. Lang and M. H. Schieber, "Reduced muscle selectivity during individuated finger movements in humans after damage to the motor cortex or corticospinal tract," J Neurophysiol, 2004, pp. 1722-1733, 91.
P. Raghavan, et al., "Patterns of impairment in digit independence after subcortical stroke," J Neurophysiol, 2006, pp. 369-378, 95.
R. Wenzelburger, et al., "Hand coordination following capsular stroke," Brain, 2005, pp. 64-74, 128.
H. Taheri, et al., "Robot-assisted Guitar Hero for finger rehabilitation after stroke," Conf Proc IEEE Eng Med Biol Soc, 2012, pp. 3911-3917, 2012.
A. S. Merians, et al., "Robotically facilitated virtual rehabilitation of arm transport integrated with finger movement in persons with hemiparesis," J Neuroeng Rehabil, 2011, p. 27, 8.
T. J. Lord, et al., "Development of a haptic keypad for training finger individuation after stroke," International Conference on Virtual Rehabilitation, Jun. 2011.
L. Connelly, et al., "A pneumatic glove and immersive virtual reality environment for hand rehabilitative training after stroke," IEEE Trans Neural Syst Rehabil Eng, 2010, pp. 551-559, 18.
R. C. Lyle, "A performance test for assessment of upper limb function in physical rehabilitation treatment and research," Int J Rehabil Res, 1981, pp. 483-492, 4.
A. R. Fugl-Meyer, et al., "The post-stroke hemiplegic patient. 1. a method for evaluation of physical performance," Scand J Rehabil Med, 1975, pp. 13-31, 7.
S. Y. Schaefer, et al., "Transfer of training between distinct motor tasks after stroke: implications for task-specific approaches to upper-extremity neurorehabilitation," Neurorehabil Neural Repair, 2013, pp. 602-612, 27.
D. T. Wade, R. Langton-Hewer, V. A. Wood, C. E. Skilbeck, and H. M. Ismail, "The hemiplegic arm after stroke: measurement and recovery," J Neurol Neurosurg Psychiatry, 1983, pp. 521-524, 46.
A. S. Go, D. Mozaffarian, V. L. Roger, E. J. Benjamin, J. D. Berry, M. J. Blaha, et al., "Heart disease and stroke statistics—2014 update: a report from the American Heart Association," Circulation, 2014, pp. e28-e292, 129.

* cited by examiner

ACTUATED GLOVE ORTHOSIS AND RELATED METHODS

CROSS REFERENCE TO RELATED APPLICATION

This application is a non-provisional that claims benefit to U.S. Provisional Patent Application No. 62/019,135 filed on Jun. 30, 2014, which is herein incorporated by reference in its entirety.

STATEMENT OF FEDERAL SUPPORT

The invention was made with government support under contract H133B031127 awarded by the National Institute on Disability and Rehabilitation Research of the Department of Education. The government has certain rights in the invention.

FIELD

This application relates generally to the field of rehabilitative devices, and particularly to systems and methods used to strengthen a person's hand.

BACKGROUND

Roughly 800,000 Americans will incur a stroke each year. While acute care and awareness of stroke symptoms have improved to the point where the one-year mortality rate has dropped to an estimated 25% of all who experience a stroke, chronic sensorimotor impairment is prevalent in a majority of the more than 6 million stroke survivors in the U.S., especially in the hand. Hands constitute our primary means of physically interacting with the external world; thus diminished control of the hand impacts all facets of life, from self-care to employment to leisure. One survey found that greater than 70% of respondents required full assistance for meal preparation, housekeeping, and laundry post-stroke. Satisfaction rates were only 14% for "vocational situation", 34% for "leisure situation", and 43% for "ability in self-care". There is a need in the rehabilitation population, including the stroke population, for systems and methods that improve the strength of a person's hand.

SUMMARY

A hand orthosis and related methods are disclosed. In an embodiment, the orthosis may comprise a finger actuation system for a finger of a human hand. The finger actuation system may comprise a digit having an opening to receive the finger; a cable guide connected to the digit and comprising at least one mechanical stop for preventing hyperextension of a joint of the finger; an actuator; and a plurality of cables inserted through the cable guide and coupled to the actuator. An actuation from the actuator creates a tension on the plurality of cables, which causes the cable guide to extend, in order to extend the finger. The actuator may provide a constant tension on the plurality of cables as the finger extends from a fully flexed position to a fully extended position.

In an embodiment, the orthosis may further comprise a second finger actuation system for a second finger of the hand, a third finger actuation system for a third finger of the hand, a fourth finger actuation system for a fourth finger of the hand, and a fifth finger actuation system for a fifth finger of the hand.

In an embodiment, the finger actuation system may further comprise a load sensor in series between the actuator and the plurality of cables for sensing the tension on the plurality of cables.

In an embodiment, the orthosis may comprise a computer for receiving information about the tension on the plurality of cables and adjusting the actuation of the actuator in response.

In an embodiment, each finger actuation system may further comprising a load sensor in series between the actuator and the plurality of cables for sensing the tension on the plurality of cables.

In an embodiment, the orthosis may further comprise a computer for receiving information about the tension on the plurality of cables and adjusting the actuation of at least one actuator in response. The computer may cause the orthosis to operate in a cyclic stretching mode. The cyclic stretching mode lasts for a period of about thirty minutes. The cyclic stretching mode may alternate between an open position cycle and a closed position cycle. The open position cycle may comprise a period of full extension for about one second at the end of the open position cycle.

In an embodiment, the orthosis may provide an increased assistance force upon detection of an EMG signal indicating extension of the finger. An actuator of the orthosis may provide a decreased assistive force upon detection of an EMG signal indicating flexion of the finger. In an embodiment, the orthosis may further comprise a transceiver for receiving a command to control the actuator and for transmitting information about the operation of the orthosis.

DETAILED DESCRIPTION

In certain embodiments, soft robotics principles may be used to provide assistance for active task practice to facilitate hand rehabilitation. As one generally sees an asymmetry in the relative deficits in voluntary digit flexion with respect to voluntary digit extension, with extension being substantially more impaired, in certain embodiments, emphasis may be placed on supporting extension of the fingers and thumb. In an embodiment, the device may either impose extension of each digit, such as to stretch the user's potentially hypertonic flexor muscles, or provide extension force to each digit, to encourage active movement. In various embodiments, an orthosis may be employed for assistive purposes as well as or in lieu of therapeutic purposes.

Figure 1A:
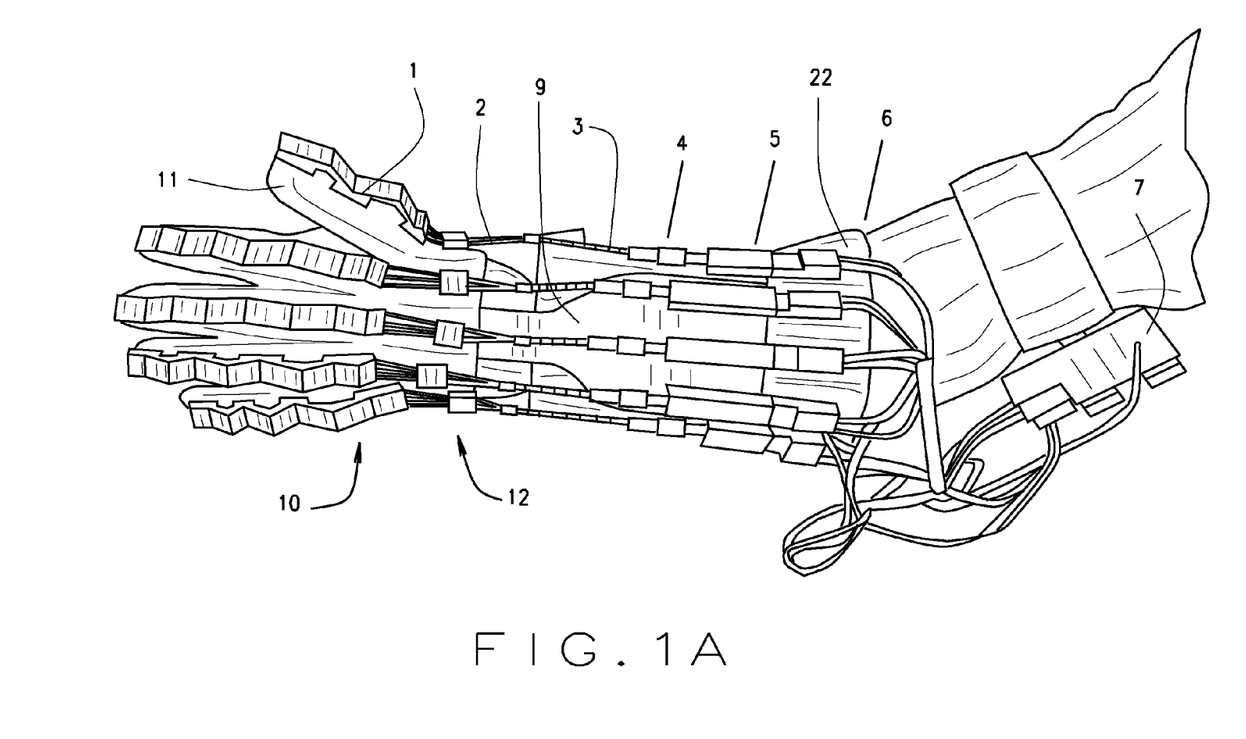
FIG. 1A shows a top view of an embodiment of an orthosis.
Figure 1B:
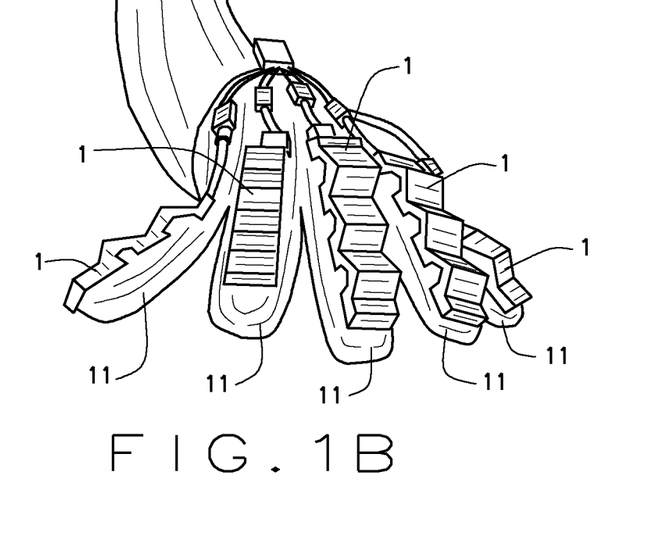
FIG. 1B shows a front view of an embodiment of an orthosis.
Figure 1C:
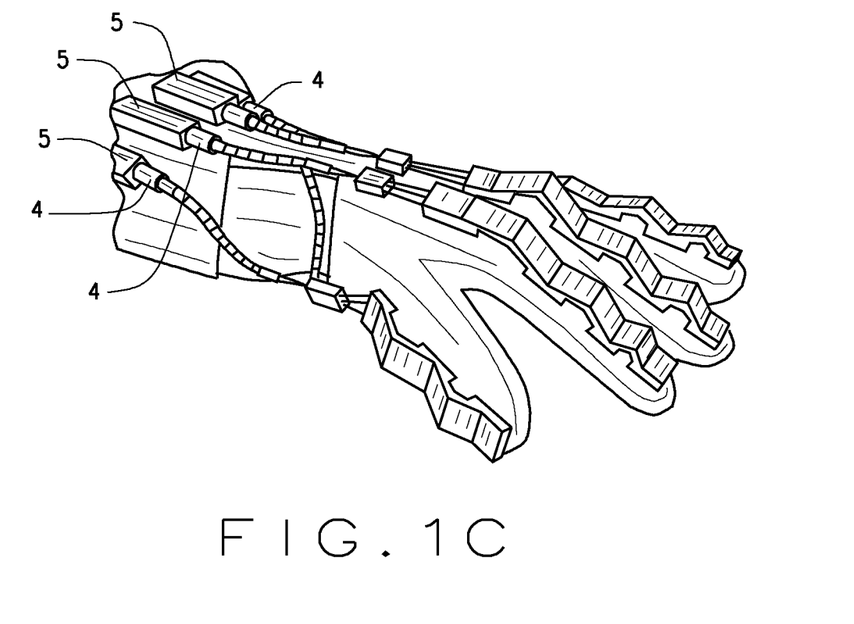
FIG. 1C shows a side view of an embodiment of an orthosis.

An embodiment of the orthosis 12 is shown in FIG. 1. The orthosis 12 may be portable. One resulting benefit is enabling the incorporation of the entire body into the therapeutic practice. Due to its design, the orthosis 12 can be used during repetitive practice of tasks important to the user with real objects. Certain functionality arises from the three main subsystems of the device, which may include actuation, sensing, and control.

Actuation

An embodiment of the orthosis 12 is shown in FIGS. 1A, 1B, and 1C. FIG. 1A shows a top view of an embodiment of the orthosis 12. FIG. 1B shows a front view of an embodiment of the orthosis 12. FIG. 1C shows a side view of an embodiment of the orthosis 12. The orthosis 12 may be used in rehabilitation or in other appropriate areas to strengthen the hand of a person who may have limited hand movement due to a stroke or other illness. In various embodiments, the orthosis may be used by those who have less than 20° of flexion contracture in any finger. The orthosis 12 comprises a glove 10 with at least one digit 11 for receipt of a user's finger. A cable guide 1 is positioned over the digit 11. The cable guide may be attached to a plurality of cables 2. The cables 2 may be attached to a connector 3, which in turn may be attached to a load cell 4. The load cell 4 is connected to an actuator 5, which is attached to a cuff 6 and also coupled by cables to a computer 7. The combination of each of these elements may be provided for each finger of the user, as shown in FIG. 1A.

Figure 2:
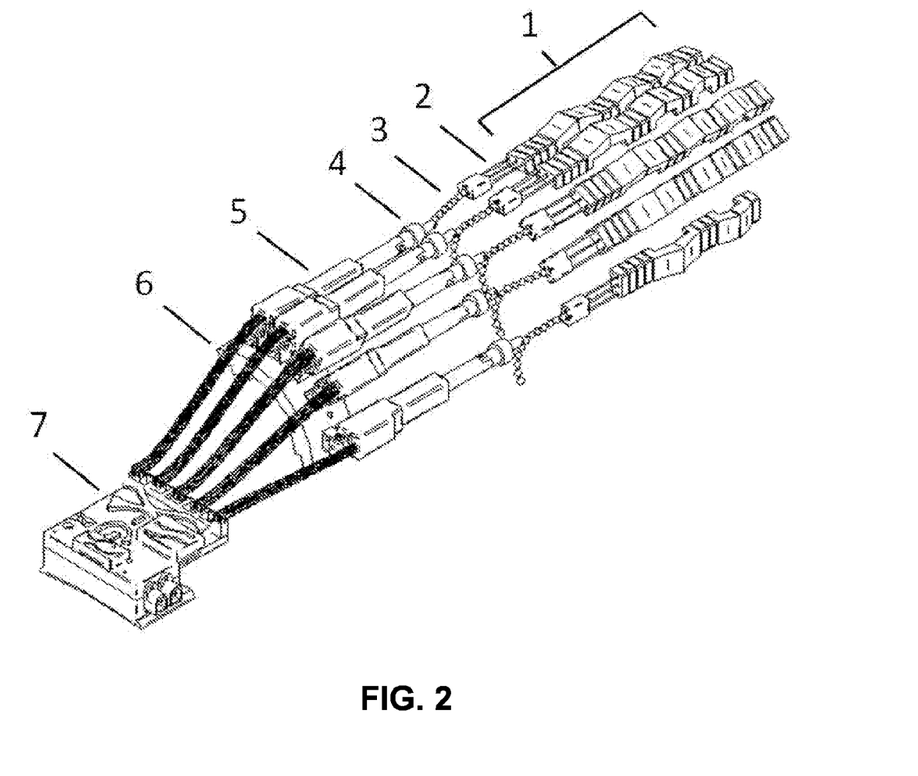
FIG. 2 shows a perspective view of an embodiment of an actuation and sensing system.

Glove 10 may be coupled to an actuation and sensing system, shown in further detail in FIG. 2. In FIG. 2, in an embodiment, cables 2 run through a cable guide 1, which may be positioned on the back of the glove 10. In one embodiment, three cables may be used. In order to minimize weight on the user's fingers, cables 2 are used to produce extension moments at each of the joints of the fingers. Cables 2 may be positioned across the back of each digit. A connector 3 enables easy separation of the glove 10 from the wrist splint to ease donning and doffing. In one embodiment, the connector 3 is comprised of a plurality of attachable bearings, similar to those used in a home light switch. The connector 3 may be attached to a load cell 4 which measures cable tension and is mounted to an actuator 5 which controls the cables 2. The actuator 5 may be a linear actuator. Each actuator 5 may be coupled to wrist splint 9, for instance through attachment to a cuff 6. Electronic components for the orthosis 12 can be housed in a computer 7 which may be worn on the user's upper arm.

In one embodiment, cables 2 may be made of Spectra kite line or another appropriate material. Cables 2 may run along the dorsal side of the glove 10 and act as a set of external extensor tendons. Pulling on the cables 2 creates extension moments which either generate digit motion or force.

The cables 2 may run through a cable guide 1, which may be custom-fabricated using selective laser sintering with a 3-dimensional printer. The cable guide 1 maintains the line of force and keeps the cables 2 from rubbing against the user's finger segments and, especially, from rubbing against the user's joints as the fingers and thumb flex.

Figure 4A:
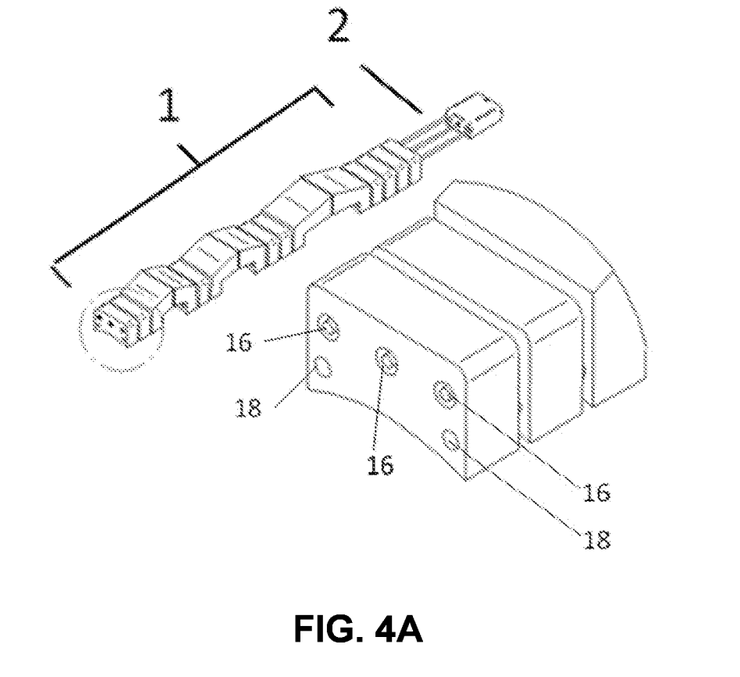
FIG. 4A shows a perspective view of an embodiment of a cable guide and cables in use with an orthosis, as well as a detailed view of an end of the cable guide.
Figure 4B:
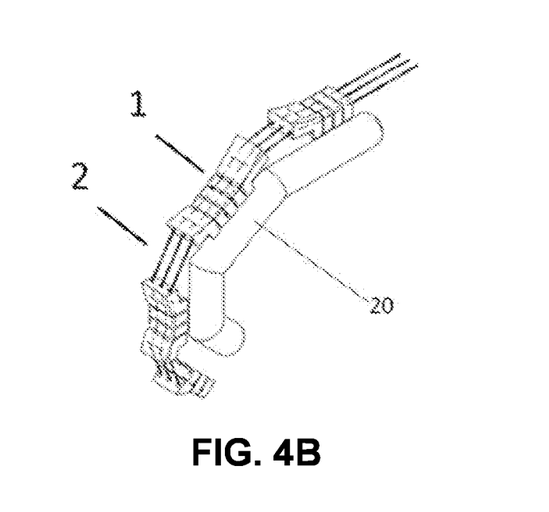
FIG. 4B shows a perspective view of an embodiment of a cable guide and cables in use with a finger.
Figure 4C:
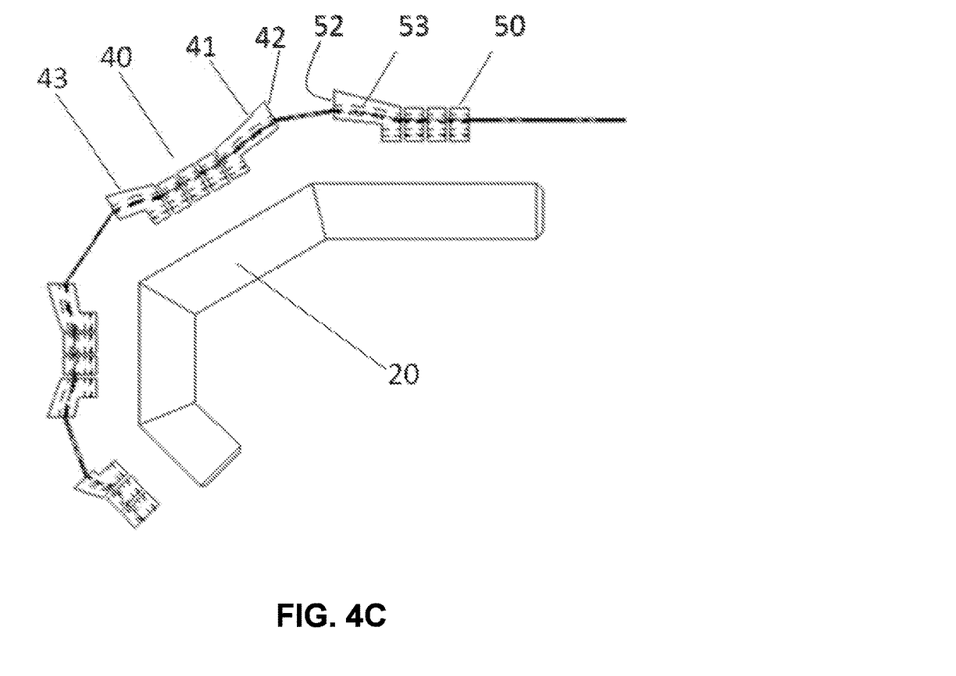
FIG. 4C shows a side view of an embodiment of a cable guide and cables in use with a finger.

Embodiments of cable guide 1 are shown in FIGS. 4A, 4B, and 4C. FIG. 4A shows an embodiment of cable guide 1 connected through cables 2. FIG. 4A also shows a detailed view of an end portion of the cable guide 1. As shown in FIG. 4A, holes 16 at the top of the cable guide 1 may provide a pathway for the cables 2 for each digit. The holes 18 at the bottom of cable guide 1 allow for the cable guide 1 to be sewn into or otherwise attached to the glove 10. The bottom of the cable guide 1 may be curved. This curvature at the bottom of the cable guide 1 provides a more comfortable fit and greater lateral stability than would a flat bottom. FIG. 4B shows a top view of the position of the cable guide 1 when the finger 20 is flexed.

Figure 4D:
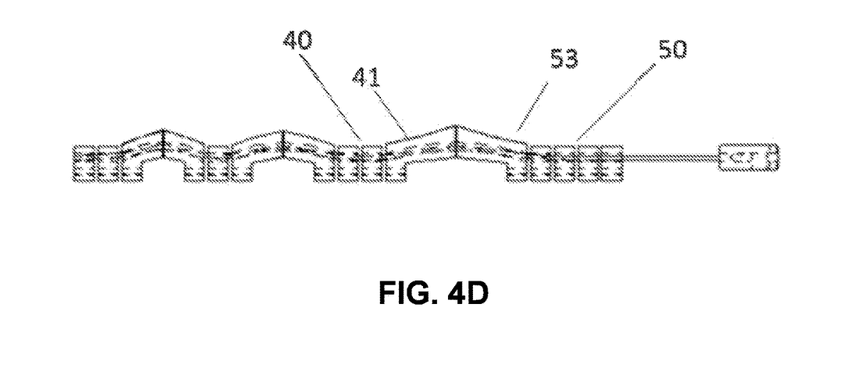
FIG. 4D shows a side view of an embodiment of extended cable guides.

The cable guide 1 also can provide mechanical stops to prevent hyperextension of the joints of a finger 20. As the pulled cables 2 will always seek the shortest path, joint hyperextension could easily result, especially if the impedance varies for different joints. In addition to leading to less functional postures, this can also be harmful to the joint, especially as stroke survivors are predisposed toward joint subluxation. FIG. 4C shows a side view of the cable guide 1 positioned over a flexed finger 20. FIG. 4C further shows a cable guide 40 comprising a proximal portion 41 and a face 42. As shown in FIG. 4C, the proximal portion 41 increases in size from its starting position in middle portion of the cable guide 40 to its end position defined by the face 42. Additionally, the proximal portion 41 so increases in size at an angle that is offset from the axis defined by the middle portion of the cable guide 40. The distal portion 43 of the cable guide 40 is similarly dimensioned, as shown in FIG. 4C, as is the distal portion 53 of cable guide 50 comprising a face 52. When the finger 20 is extended, face 42 pairs with face 52 such that proximal portion 41 and distal portion 53 push against each other, as shown in FIG. 4D. This forms a bridge-like structure when the joint is extended, thereby preventing further rotation. This bridge-like design for specific pairs of adjacent cable guides can help to prevent joint hyperextension, which can damage the user's joint.

The bottom of each cable guide 1 may be curved to better match the shape of the user's finger 20 and for greater lateral stability and comfort. Holes in the cable guide 1 can allow the cables 2 to pass through the cable guides 1. In one embodiment, the cable guide 1 may be made of a glass-filled nylon material. Use of this material, and of kite line material for the cables 2, can minimize frictional losses. In an embodiment, three cables 2 run in parallel across the dorsal side of each digit. The three cables 2 help to further stabilize the cable guide 1 and prevent rotation about the long axis of the finger 20.

Another set of holes in each cable guide 3 permits the cable guide 3 to be sewn directly into a modified sports glove 10. The glove 10 may be fabricated primarily from leather but with compliant material over the dorsal side of each joint to accommodate length changes required by the rotating joint. A custom zipper may be sewn into the palmar side of the glove in order to ease donning of the glove. The zipper can run across the metacarpophalangeal (MCP) joints of the fingers and down the ulnar side of the palm.

The back side of the glove 10 may contain a pocket into which the end of the splint 9 can be inserted. The splint 9 may extend across the wrist and onto the forearm, about which it may be secured with a strap. The splint 9 may maintain the wrist in a neutral posture, which can be beneficial for grasping and also can preclude wrist movement which could interfere with operation of the orthosis 12.

For each digit, the cables 2 can converge to a single cable proximal to the metacarpophalangeal (MCP) joint. This cable may end in a connector 3 to allow for rapid attachment and detachment of the glove from the rest of the device in order to facilitate donning and doffing of the orthosis 12.

Figure 3A:
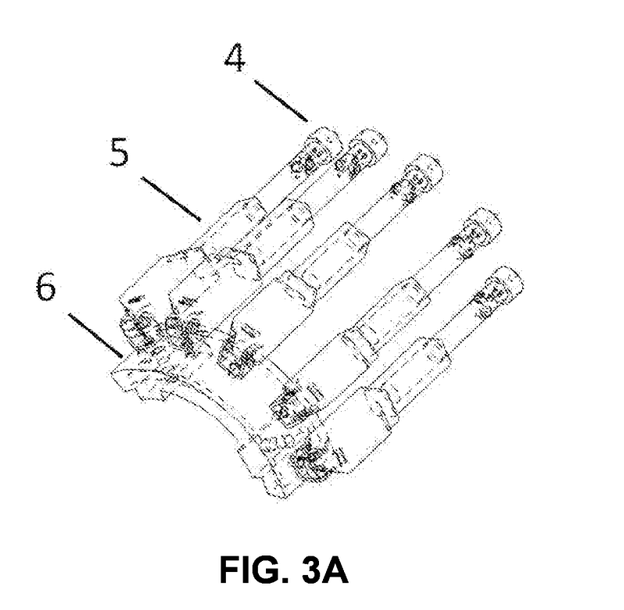
FIG. 3A shows an exploded view of a portion of an embodiment of an actuation and sensing system.
Figure 3B:
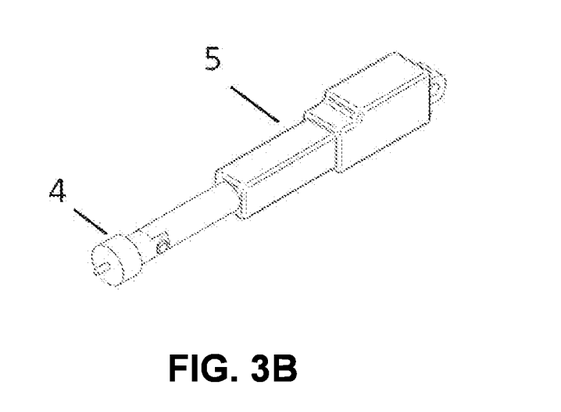
FIG. 3B shows a perspective view of an embodiment of an actuator and load cell.

The connector 3 may link the cables with the linear actuator powering the digit, as shown in FIG. 3A. The actuator 5 (which may be a L12, Firgelli Inc., Surrey, Canada) can be positioned in series with the connector 3. Connection of the actuator 5 to the cuff 6 allows the actuator 5 to pivot to maintain alignment with the finger 20. The cuff 6 can be readily moved from one wrist splint 9 to another. FIG. 3B provides a closer view of a single actuator 5 and load cell 4.

Figure 5:
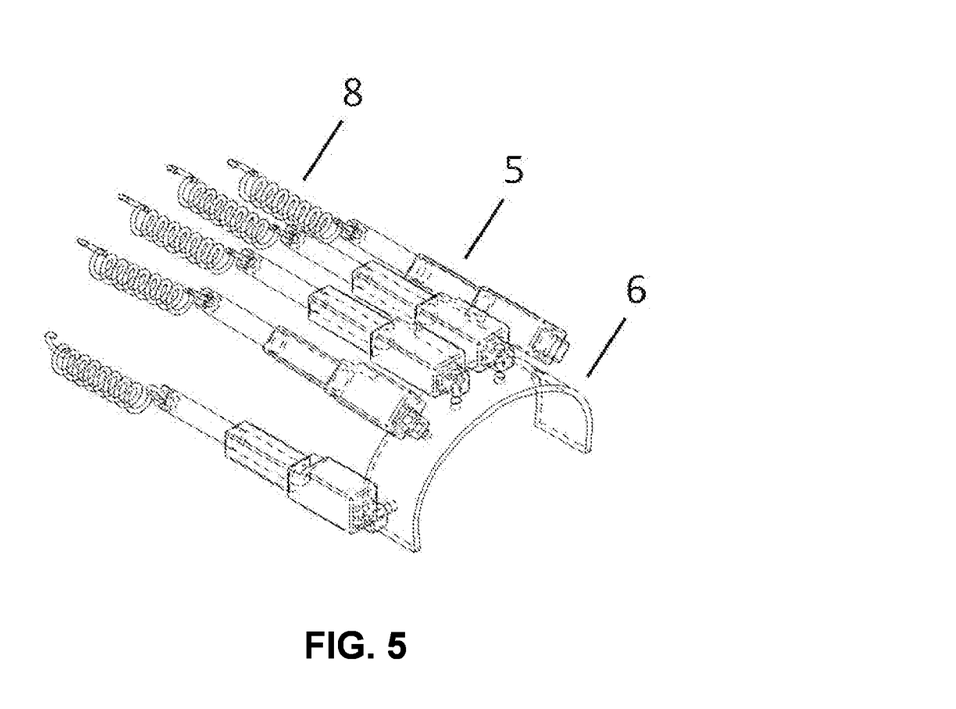
FIG. 5 shows a perspective view of an embodiment of an orthosis comprising a plurality of springs.

Additionally, or in another embodiment, a spring 8 can also be inserted between the actuator 5 and the connector 3, as shown in FIG. 5. Including the spring 8 provides for series elastic modulation. Retraction of the actuator 5 produces extension of the joints of the finger 20 and extension of the actuator permits the user to flex her joints on finger 20. A combination of actuator stroke lengths is utilized (such as 30 mm and 50 mm) to allow full flexion and extension of each finger 20. The actuators may be connected to the splint 9 through a pin joint, which permits rotation to align the motor with the finger 20.

Sensing.

Cable displacement and force may be measured in control of the orthosis 12. Cable displacement may be determined by the movement of the actuator 5 for each digit. This information can be read directly from the output of the actuator 5 into a microcontroller 30, which may be 32-bit or 64-bit, or another appropriate configuration. The microcontroller may have a memory portion for storing instructions and a processor portion for executing instructions. In an embodiment, the microcontroller 30 may be a RabbitCore microcontroller (RCM 3410; Digi International, Inc.) configured using known methods to read in force data supplied by a load cell 4 and also configured to generate the appropriate Pulse Width Modulation (PWM) signal for the actuator 5.

Cable force can be measured in each of cables 2 with a load cell 4 connected in series with the cables 2 and the actuator 5. Each miniature load cell 4 (which may be Model 11, Honeywell Sensotec) can measure tensile force in each cables 2 over the required range. Signals may be buffered and filtered in hardware prior to sampling with the microcontroller 30.

In various embodiments, the orthosis 12 may be configured so that the actuator 5 stops providing an extension force when the user wishes to close her hand. For example, it may be desirable for the actuator 5 to stop moving when the user's finger 20 starts to flex to a closed position, so that the user does not need to overcome the force provided by the actuator 5 in order to flex the finger 20. This feature may be particularly helpful for the treatment of stroke patients, who are able to close their hand but have difficulties, post-stroke, opening their hand.

For example, an electromyographic (EMG) system may be employed to permit EMG-driven control of the orthosis 12. In one embodiment, shown in FIG. 7, electrodes 60 may be so positioned as to detect EMG signals from the user's finger 20. Electrodes 60 may comprise standard surface electrodes. Alternately, electrodes 60 may be electrodes that are connected to the splint 9 and its strap. The electrodes 60 may receive an EMG signal and provide it to an electronics board 34 for further processing. For instance, the EMG signal may be amplified with amplifier 37 (which may be an instrumentation amplifier) and filtered using a filter 38 (which may be an active, lowpass Butterworth filter). Full-wave rectification may be performed in hardware (for instance, through diodes 39) followed by lowpass filtering (for instance, through Butterworth filter 31) to create an envelope for the EMG signal. The envelope may subsequently be sampled by the microcontroller 30. For instance, the microcontroller 30 may sample for a threshold value on the envelope. Alternatively, the rectification and filtering could be performed in software stored and executed with the microcontroller 30. In this embodiment, an analog front-end receives the data from electrodes 60 and provides it to the microcontroller 30.

Figure 7:
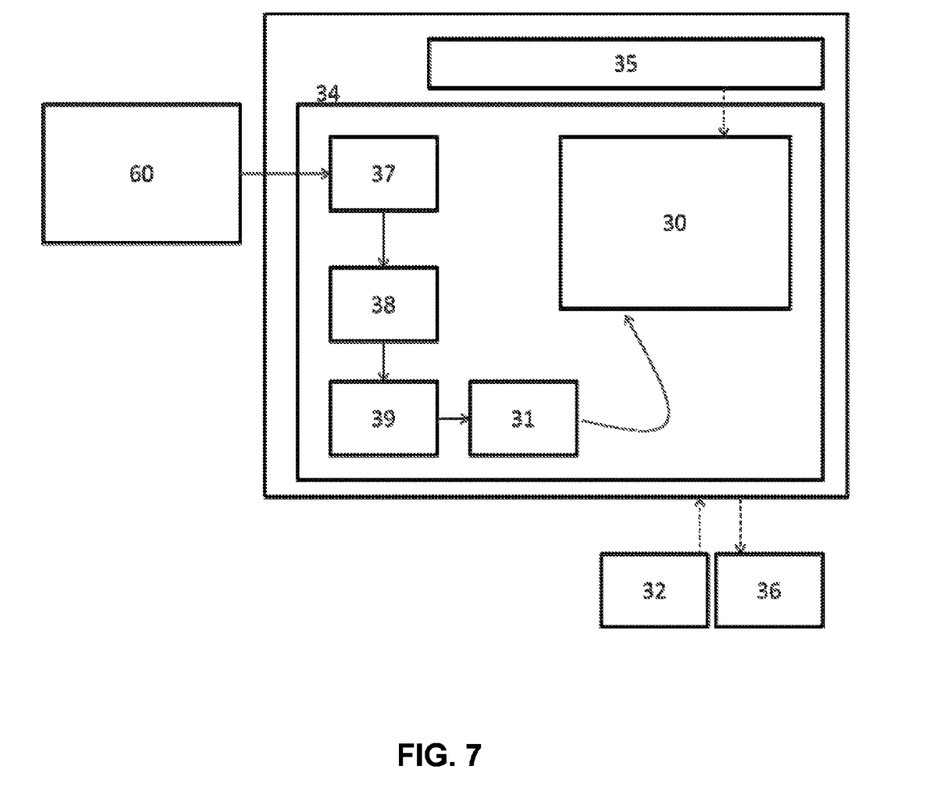
FIG. 7 shows a diagram of an embodiment of a computer and related elements that may be used with an orthosis.

The electronics board 34 may be housed in a computer 7 which can be worn on the user's arm. Alternatively, the electronics board 34 could be incorporated into the splint 9. One or more push buttons 36 coupled to the computer 7 can allow the user to provide input, such as switching among different modes. Computer 7 may comprise a transceiver 35, allowing data to be transmitted wirelessly from the computer 7 to an external computer or a smart device (such as a mobile phone running an Android®, Apple®, or other operating system) for storage and analysis. Data can also be displayed locally on a small display 36 coupled to the computer 7 to provide feedback on force and position for each digit of orthosis 12.

The orthosis 12 may be battery driven, with the battery located either on a belt or in the computer 7, allowing the orthosis 12 to be portable. For instance, the battery may be a 2-cell lithium ion battery.

Control.

Movement of each actuator 5 may be controlled by the microcontroller 30, for instance using pulse-width modulation (PWM). Stroke position of the actuator 5 may be proportional to the duty cycle of a 1 kHz square wave. Maximum speed of travel can be determined by the gearing of the actuator 5 and the load or force that the actuator 5 is working against at a given moment in time. In one embodiment, the gearing reduction ratio may be 1:100, the maximum speed of the actuator 5 may be 12 mm/s, and the maximum force it can provide may be 80N.

Modes of Operation.

The orthosis 12 can be used in one of multiple modes as selected by the user. A first mode may comprise one or more cycles of stretching. For example, the mode may comprise repetitive, cyclic stretching, which has been found to be beneficial in stroke survivors. Each of the five digits can be moved through its range of motion, as set by the push of a button coupled to the orthosis 12, or utilizing a voice recognition chipset integrated into the computer 7. Each digit 11 may be moved by its respective actuator 5 from an initial, flexed resting posture to the extension limit. Each digit 11 may be held in this extended posture and then allowed to flex again back to the resting posture. Stretching speed, frequency, and duration can be set within the system, for instance through the microcontroller 30. A slow movement (cable displacement of 4 mm/s or less) may be imposed to preclude any spastic response due to the stretching. For example, a user may use the orthosis 12 for a session. For a period of about thirty minutes during the session, the orthosis 12 may cyclically stretch one or more of the user's finger flexors (including the thumb flexor) while the user remains relaxed. Each cycle may last about 15 seconds in an open position cycle (in which the actuator 5 provides extension assistance to open the user's hand until the finger 20 moves to a fully flexed position) and about 15 seconds in a closed position cycle (in which the actuator 5 provides no extension assistance and the user closes her hand until the finger 20 moves to a fully flexed position). This results in approximately 120 open/close cycles throughout the 30 minute session. In the open position cycle, the fingers 20 may be held in fully extended position for about 1 second before beginning to return to a flexed posture. A "fully extended position" is the position of the finger 20 when the finger is fully extended and a "fully flexed position" is the position of the finger 20 when the finger is fully flexed. These positions may be different for different users of the orthosis 12, depending on their strength, the severity of their stroke or other disease, or other factors.

The orthosis 12 can also be used to in another mode in which the orthosis 12 provides extension assistance, as needed, to increase finger movement. When used in this mode, the orthosis 12 can promote active training of finger movement. Constant extension assistance provided to each digit 11 may increase the active range of motion and reduce movement error. Periodically during the therapy session, the user will be instructed to relax. The orthosis 12 will then pull each digit 11 into full extension and measure the corresponding cable force in each digit 11. The measured amount is the amount of constant extension assistance that the orthosis 12 will provide. In this way, the user can close his or her hand only by flexing his or her fingers with a force that is greater than the extension force provided by the orthosis 12. The amount of flexion force the user is required to provide does not increase with greater flexion of the fingers, as is true with other systems that employ springs to resist the user's flexion force. (In fact, this has been shown to be detrimental to the user's active range of motion.) Instead, the extension force provided by orthosis 12 remains constant regardless of how far the user has flexed his or her fingers.

In one embodiment, a Proportional-Derivative (PD) control strategy can be used to maintain this constant extension force. The desired force constitutes the system input, which is compared to the actual tension on cables 2 as measured with the load cell 4. The resulting error signal is sent through a PD module that may be stored and executed on the microcontroller 30. The PD module may generate the driving signal, which is subsequently translated into the appropriate PWM signal by a module executed on the microcontroller 30, to increase or decrease tension on the cables 2. As the motor for each digit is controlled independently, digits can be allowed to move freely or locked in place to permit focusing on a subset of the digits.

Figure 6:
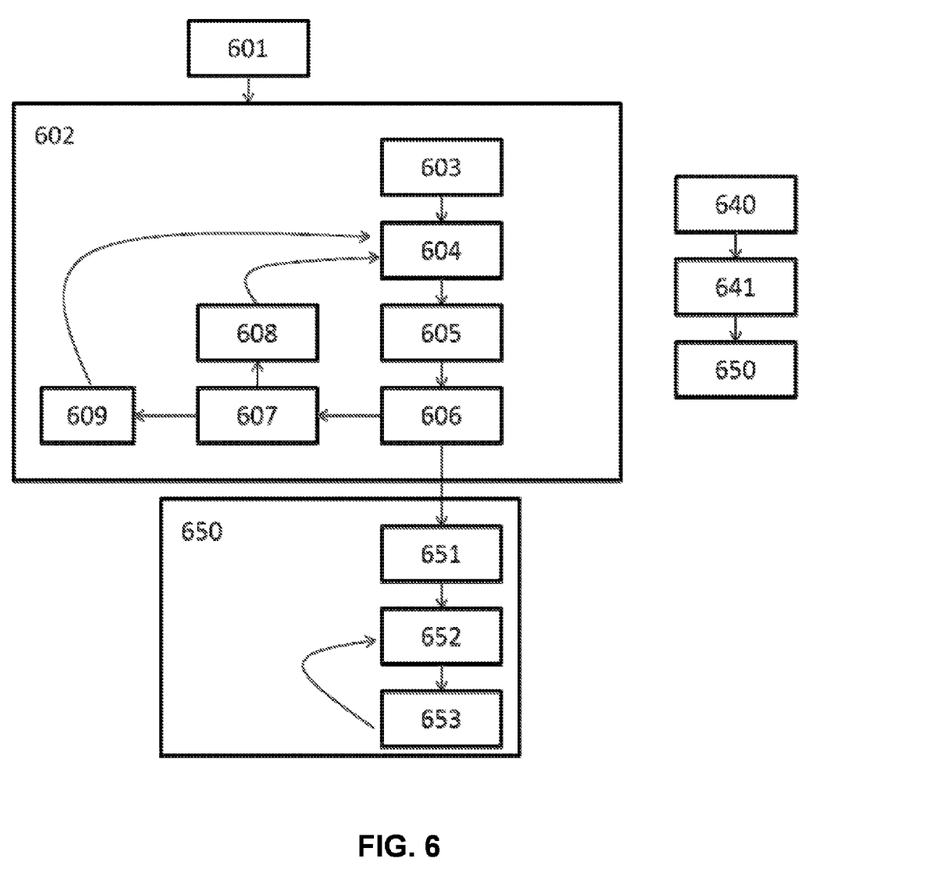
FIG. 6 shows a flowchart for exemplary control of an orthosis.

FIG. 6 shows a flowchart for one possible method of control of the orthosis 12. In 601, the orthosis 12 may be initialized. In 602, the orthosis 12 may move into a mode of passive stetching. In 603, the orthosis 12 may begin to provide extension assistance. In 604, the orthosis 12 may set the PWM command to actuate one or more actuators 5. In 605, the orthosis 12 delays, for example for about one second. In 606, the orthosis 12 checks whether the period that has elapsed is more than the set time. If the period has elapsed, the orthosis 12 may switch to a mode of active training 650. If the period has not elapsed, in 607 the orthosis checks whether the actuator 5 has reached 100% extension. If it has, in 608 the orthosis 12 decreases the duty cycle of the actuator 5, for instance by 12.5%. If it has not, in 609 the orthosis increases the duty cycle of the actuator 5, for instance by 12.5%.

They system may provide for an interruption event 640. In 641, if a button 32 is pressed, then the orthosis 12 switches to a mode of active training 650.

In active training 650, the orthosis may retract the actuator 5 and measure the desired constant force, as indicated by 651. In 652, the orthosis 12 checks whether the actual force is greater than the desired force, and continues to check until the actual force is greater than the desired force. When that condition is true, in 653 the orthosis 12 applies the PD controller gains and causes actuation of the actuator 5.

One course of therapy is to combine cyclic stretching with active training. Stretching is applied for a desired period of time immediately prior to engaging in task training with extension compensation. Stretching sessions can also be interjected into the active training as deemed appropriate by the therapist.

It should be understood that the present disclosure sufficiently describes the orthosis 12 such that other uses may be employed. For example, using EMG, EEG, or voice control the user could vary the amount of extension assistance provided by the orthosis 12, such that extension assistance decreases during intended flexion and increases during intended extension. For instance, the user may say "close" out loud, which causes the actuators 5 to stop actuating, therefore allowing the user to close her hand without having to overcome force from the motors.

Various methods may be employed in using the orthosis 12. For example, combining passive cyclical stretching (reducing motoneuronal hyperexcitability) imposed by the orthosis 12 with active-assisted, task-oriented training (rehabilitating muscle activation) can improve upper extremity motor control and task performance after a user has had a stroke. In one of our recent studies, thirteen participants who experienced a stroke 2-6 months prior to enrollment completed 15 treatment sessions over 5 weeks. Each session involved cyclically stretching the long finger flexors (30-min) followed by active-assisted task-oriented movement practice (60-min). Outcome measures were completed at 6 intervals: three before and three after treatment initiation. Overall improvement in post-training scores was observed across all outcome measures, including the Graded Wolf Motor Function Test, Action Research Arm Test, and grip and pinch strength ($p \leq 0.02$), except finger extension force. No significant change in spasticity was observed. Improvement in upper extremity capabilities is achievable for stroke survivors even with severe hand impairment through an intervention combining passive cyclical stretching and active-assisted task practice. This paradigm is simple to incorporate into clinical practice.

Each user participated in up to three 90-minute sessions per week, for a total of 15 training sessions. For the first 30 minutes of each session, the orthosis 12 cyclically stretched the thumb and finger flexors while the user remained relaxed. Each cycle lasted roughly 15 seconds, resulting in approximately 120 open/close cycles throughout the 30-min stretching session.

Immediately afterward, users employed the orthosis 12 for 60 minutes of active training guided by a research occupational therapist using a task-oriented protocol. In this therapy protocol, participants were encouraged to perform high repetitions of tasks, task components, and performance skills focused mainly on the hand. As part of the protocol, the Canadian Occupational Performance Measure (COPM) may be administered to identify goals that incorporated use of the affected hand. Part of each training session was used to practice these tasks, while the remainder was used to practice component skills. The occupational therapist may provide feedback to the user regarding performance and graded tasks as well as the environment as needed to optimize challenge. The therapist recorded total repetitions completed during each session.

Clinical task performance may be evaluated with the Action Research Arm Test (ARAT), the Graded Wolf Motor Function Test (GWMFT), and the Chedoke Arm and Hand Inventory (CAHAI-9). Impairment may be evaluated with the Fugl-Meyer Assessment for Motor Recovery after Stroke for the Upper Extremity (FMUE) and hand strength assessments. For the latter, the 3-point palmar (PPS) and lateral pinch strengths (LPS) may be measured with a pinch gauge (PG-60, B&L Engineering), grip strength (GS) may be quantified with a dynamometer (JAMAR 5030J1 Hand Dynamometer), and finger extension force (EXT) may be recorded with a digital force gauge (Mark-10 Corp. MG200). Additional outcome measures may be included to further examine effects of the treatment. They may consist of the Modified Modified Ashworth Scale (MMAS) or the Motor Activity Log (MAL). The MAL may be administered once prior to treatment, immediately following treatment, and later, such as one-month later. Despite substantial hand impairment, users may average over 160 hand movements per training session, a number that far exceeds the number expected in a typical therapy session in a clinic.

Various protocol methods may be used. The methods set out here may be performed in the sequence in which they are described, or in other sequences. All or a subset of the methods may be performed for any particular user. The use of the word "subject" in this section refers to the user of the orthosis 12.

Prefunctional activities may comprise distal exercises. For example, the following methods may be employed: Gross finger flexion and extension exercises; individual finger flexion and extension exercises (may include blocking exercises); Isometric holds for finger extension; Finger abduction/adduction; Exercises for lumbricals (start out in full finger flexion and assume intrinsic plus position); exercises for thumb in all planes; opposition of thumb to all digits, with isotonic holds using objects between thumb and digit; lift fingers off table individually; Practice finger tapping—use all four fingers and then one at a time; Increase strength of intrinsics (lumbricals, abductors, and adductors) as needed. Start with placing hand in position and asking subject to hold; passive stretch supination; and active assist supination/pronation.

Activities to promote grasp and release may be employed. For example, for grasp the following methods may be employed: Strengthen weak grasp by pulling a rolled towel through the hand in radial direction and asking the subject to squeeze and then release; Practice holding forearm in neutral position while supported by table; Practice holding object that is placed in hand by therapist while arm is supported by table (can use any type of grasp or pinch); Placed object in subject's hand and practice holding close to body while standing/walking; Practice moving the arm with object placed in hand(s) with arm supported on table (with and without vision); Place object in subject's hand(s) and practice holding free in space; Hold onto jar with affected hand and unscrew lid with unaffected one (required task for individuals with affected non-dominant hand); and place object in subject's hand (subject can also place it with unaffected hand) and change weight of object (pour water into a cup, add items to a tray.

Also for grasp, the following methods may be employed: Strengthen thumb in radial abduction to increase stability; Subject opens hand to grasp and hold object, moves thumb up and down object surface while maintaining grasp, then releases object on table top; Subject opens hand to grasp small pill bottle in hand and uses thumb to lift lid while maintaining grasp, then release bottle onto table top; Grasp object on table that is supported by therapist (therapist is holding/stabilizing the object); Grasp bean bag on table; Crumple up a sheet of newspaper into a small ball with one hand; Grasp object without support by therapist; Grasp object with eyes closed (may help increase hand opening); Train grasp/pinch using a variety of objects; Grasp an object and then change the weight of it (e.g. grasp a cup and therapist can pour liquid into it or subject can pour with unaffected hand); Train to grasp an object and then rotate it (e.g. pick up box of cereal and then rotate box to pour cereal in bowl); Work on repetitive grasp and release of one object increasing speed.

For force modulation and grip lift, the following methods may be employed: Hold object in unaffected hand lift off of table, then attempt with affected hand; Place object in subject's hand, which is lifted off table. Subject attempts to hold objects while elbow is on table; Subject grasps or places object requiring bilateral use in both hands with forearm free in space. For force modulation and grip lift, the following methods also may be employed: Train to grip dynamometer, pinch meter, blood pressure cuff or any instrument with visual feedback to vary levels of force and release; In standing, reach for object on table (table must be raised or can use a box or shelf). Press down into table prior to lift off; Hold a squeeze bottle/coffee sleeve/plastic cup and squeeze then open fingers slightly without dropping or crushing.

For release, the following methods may be employed: Practice holding 1 or 2 lb weight in hand and then lowering it onto mat or floor and releasing (holding weight enables relaxation of long finger flexors). Thumb should be in extended position. Forearm can be neutral or pronated; After grasping rolled towel, relax finger flexors. Therapist can position towel in the air so that subject's arm is slightly raised. Use gravity. Practice holding a large ball with two hands and then letting go; Pass object from one hand to another; Release of a supported object on table following pronated grasp by using tenodesis effect.

For release, the following methods also may be employed: Release of a medium width cylindrical object (can or glass) that is externally supported (on table or countertop) and with the therapist's hand stabilizing the object. Therapist's hand should be on top of the can while the subject attempts to release his/her hand, which is gripping sides of can. Therapist maintains hold on can while subject releases. Task will be easiest at this level since less force modulation is required for this task; The same as the prior method, but with different object widths; the same as the prior methods, but using grasp with forearm in neutral; Release of an unsupported object but subject's arm is supported by table; Release of small ball onto floor using increased velocity; Release of objects using two targets of different height (e.g. shelves); Transport an object and then release.

For activities to promote reach to grasp sequence, the following methods may be employed: Subject uses both hands to push wheelchair or cart (hands grasping handle, forearm in neutral position and/or pronated); Subject is sitting and reaches to down to target close to floor. Gravity may help to release tone. Object is placed in hand by therapist. Subject grasps it and brings it up to lap; Place hand on faucet with arm supported on sink and practice turning water off and on; Train the affected arm to reach and point without grasp to a target while the arm is fully supported on a table. Start this task by positioning target in the unaffected space (affected arm uses adduction and crosses midline). Progress to reaching straight forward in line with the shoulder while arm is supported on table; Reach away from midline with shoulder abduction while arm is supported on table; Open hand, wipe a table using horizontal adduction and abduction; Subject holds on to handle of pan or other object and slidesit across table, then release; Train hand to mouth movement while holding a cup unilaterally. Use different types of cups including plastic drinking glass, paper cup, and coffee cup w/ and w/o liquid; Train eccentric control of reach with object placed in hand; Open hand to grasp cup, train hand to mouth movement while holding a cup unilaterally, then release cup to tabletop. Use different types of cups including plastic drinking glass, paper cup and coffee cup w/ and w/o liquid; Use affected arm to open/close door. Hand can be placed on handle, or handle can be grasped. Can use simulated door handle on box; Open close drawer with affected hand. Hand position above; Practice reaching and turning on light switch (can use unrefined grasp); Train to move arm free in space with object already placed in hand; As the prior method but with bilateral use (ex. Tennis racket, golf club); Work on shoulder and elbow control in supine (place and hold, active assist, reach to target); Practice elbow extension in sitting with the hand of the affected arm fixed on the mat; Work in sitting/side lying/supine or prone on concentric and eccentric shoulder flexion (begin with place and hold and progress to stop and hold); Throw beanbag towards feet after retrieving it from opposite shoulder.

For activities to promote reach to grasp sequence, the following methods also may be employed: Work on reaching to target which is visible but with no vision of the arm; Work on reaching to various targets using slow movements interspersed with fast reaching movements; Work on reaching across midline (using shoulder adduction) and grasping an object with arm free in space and release; Work on reaching in sagittal plane (arm in line with shoulder) and grasping an object with arm free in space and release; Work on reaching away from midline and grasping an object with arm free in space and release.

For fine motor activites, the following methods may be employed. For three jaw chuck: 1. Hold sugar packet with affected hand; practice opening packet 2. Practice picking up salt shaker, turning over and gently shaking. 3. Pick up blocks/checkers/dice and release. 4. Grasp, pinch and release large clips on the edge of a box. For lateral pinch: Practice pouring from a container with a handle (tea kettle or pitcher); Practice placing envelopes in simulated mail slot on box; Set a table using affected hand to place flatware; Practice counting bills while holding bills with unaffected hand; Practice putting key into lock; Practice opening door with key; Practice zipping and unzipping on dressing board, clothing, pocket book, etc; Practice unwrapping thread around spool using affected hand to hold thread (can downgrade by using yarn); Play cards shuffling and dealing; Pick up a card from edge of a raised surface/box and release; Practice opening up containers with small lids (soda bottles); Hold and drink with cup with handle; File nails with emery board; Cut with large scissors; Cut with small scissors; Pinch, place and release close pins; Practice pulling cap off pen; Use butter knife to cut bread (can substitute Theraputty). Can also spread butter on bread.

For tripod, the following methods may be employed: 1. Practice tracing. 2. Practice drawing shapes. 3. Practice writing. 4. Practice drawing with a guide (ruler or stencil). 5. Practice using fork or spoon during feeding.

Methods may be used to give therapists a greater variety of activities from which to choose to best matches a user's ability level. AS the deficits from stroke are not uniform and recovery of motor skills is not ordinal, there is a spectrum of ability levels that present as a Stage 4 on the Chedoke McMaster Stroke Assessment. In order to best accommodate the varying abilities or upgrade difficulty when a user has improvements, activities from additional stages may be included.

What is claimed is:

1. An orthosis, comprising:
    a. a finger actuation system for a finger of a person's hand, comprising:
        i. a digit having an opening to receive the finger;
        ii. a cable guide connected to the digit and comprising at least one joint hyperextension mechanical stop;
        iii. an actuator for applying tension on a plurality of cables;
        iv. the plurality of cables inserted through the cable guide and coupled to the actuator;
        v. a control system for controlling the operation of the actuator and measuring the amount of tension needed to fully extend the digit when the user is in a relaxed state;
        vi. wherein the control system actuates the actuator to create a tension on the plurality of cables, which causes the cable guide to extend, in order to extend the finger;
        vii. wherein in one mode of the control system, the actuator is actuated to apply a constant extension force on the plurality of cables as the finger extends from a fully flexed position to a fully extended position, the constant extension force determined by the measured tension when the user is in the relaxed state; and
        vii. wherein the control system further allows voluntary finger flexion when the user exerts a voluntary flexion force that exceeds the applied extension force.

2. The orthosis of claim 1, further comprising a second finger actuation system for a second finger of the hand, a third finger actuation system for a third finger of the hand, a fourth finger actuation system for a fourth finger of the hand, and a fifth finger actuation system for a fifth finger of the hand, wherein each of the second, third, fourth, and fifth finger actuation systems comprise each limitation of the finger actuation system.

3. The orthosis of claim 1, wherein the finger actuation system further comprises a load sensor in series between the actuator and the plurality of cables for sensing the tension on the plurality of cables.

4. The orthosis of claim 1, further comprising a computer for receiving information about the tension on the plurality of cables and adjusting the actuation of the actuator in response.

5. The orthosis of claim 2, each finger actuation system further comprising a load sensor in series between the actuator and the plurality of cables for sensing the tension on the plurality of cables.

6. The orthosis of claim 2, further comprising a computer for receiving information about the tension on the plurality of cables and adjusting the actuation of at least one actuator in response.

7. The orthosis of claim 6, wherein the computer causes the orthosis to operate in a cyclic stretching mode.

8. The orthosis of claim 7, wherein the cyclic stretching mode lasts for a period of about thirty minutes.

9. The orthosis of claim 7, wherein the cyclic stretching mode alternates between an open position cycle and a closed position cycle.

10. The orthosis of claim 9, wherein the open position cycle comprises a period of full extension for about one second at the end of the open position cycle.

11. The orthosis of claim 1, wherein the orthosis provides an increased assistance force upon detection of an EMG signal indicating extension of the finger.

12. The orthosis of claim 1, wherein the actuator provides a decreased assistive force upon detection of an EMG signal indicating flexion of the finger.

13. The orthosis of claim 4, further comprising a transceiver for receiving a command to control the actuator and for transmitting information about the operation of the orthosis.

14. The orthosis of claim 1, further comprising:
an additional cable guide positioned along the plurality of cables a predetermined distance from the cable guide;
wherein a face defined by the cable guide is oriented towards a face defined by the additional cable guide, wherein both faces collectively define the joint hyperextension mechanical stop.

15. The orthosis of claim 1 having at least two cable guides positioned along a back of the digit of the orthosis adjacent to one another, each cable guide comprising at one end a proximal portion defining a proximal face and at the opposite end a distal portion defining a distal face, the mating of a distal face of one cable guide with the proximal face of the adjacent cable guide comprising the at least one hypertension mechanical stop.

16. The orthosis of claim 15 wherein the mating of the faces of adjacent cable guides form a structure in the shape of a bridge.

17. The orthosis of claim 15 wherein the mating of the faces of adjacent cable guides results when the finger in the digit of the glove is extended.

* * * * *